(12) United States Patent
Raines et al.

(10) Patent No.: US 6,871,838 B2
(45) Date of Patent: Mar. 29, 2005

(54) INJECTION PORT VALVE

(75) Inventors: Kenneth C. Raines, Bethlehem, PA (US); Joel M. Bartholomew, Danielsvile, PA (US); Peter W. Peppel, Nazareth, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 14 days.

(21) Appl. No.: 10/407,001

(22) Filed: Apr. 3, 2003

(65) Prior Publication Data
US 2004/0195538 A1 Oct. 7, 2004

(51) Int. Cl.⁷ .......................... F16K 51/00; F16L 29/00; F16L 37/28
(52) U.S. Cl. ................... 251/149.4; 251/149.1; 251/149
(58) Field of Search ........................ 251/149, 149.1, 251/149.4, 149.6, 335.1, 335.2, 335.3, 337; 137/625.4, 602

(56) References Cited

U.S. PATENT DOCUMENTS

| | | |
|---|---|---|
| 3,570,484 A | 3/1971 | Steer et al. |
| 3,806,086 A | 4/1974 | Cloyd |
| 4,883,467 A | 11/1989 | Franetzki et al. |
| 4,934,655 A | 6/1990 | Blenkush et al. |
| 4,953,594 A | 9/1990 | Von Berg |
| 5,104,389 A | 4/1992 | Deem et al. |
| 5,163,922 A | 11/1992 | McElveen, Jr. et al. |
| 5,190,523 A | 3/1993 | Lindmayer |
| 5,203,775 A | 4/1993 | Frank et al. |
| 5,230,706 A | 7/1993 | Duquette |
| 5,242,393 A | 9/1993 | Brimhall et al. |
| 5,242,423 A | 9/1993 | Goodsir et al. |
| 5,251,873 A | 10/1993 | Atkinson et al. |
| 5,269,771 A | 12/1993 | Thomas et al. |
| 5,289,849 A | 3/1994 | Paradis |
| 5,322,516 A | 6/1994 | Brugger |
| 5,336,174 A | 8/1994 | Daoud et al. |
| 5,353,837 A | 10/1994 | Faust |
| 5,360,413 A | 11/1994 | Leason et al. |
| 5,390,898 A | 2/1995 | Smedley et al. |
| 5,395,348 A | 3/1995 | Ryan |
| 5,401,245 A | 3/1995 | Haining |
| 5,409,463 A | 4/1995 | Thomas et al. |
| 5,251,873 A | 5/1995 | Atkinson et al. |
| 5,423,791 A | 6/1995 | Bartlett |
| 5,425,465 A | 6/1995 | Healy |
| 5,439,451 A * | 8/1995 | Collinson et al. ........... 604/247 |
| 5,441,487 A | 8/1995 | Vedder |

(Continued)

Primary Examiner—Edward K. Look
Assistant Examiner—John K. Fristoe, Jr.
(74) Attorney, Agent, or Firm—Christie, Parker & Hale, LLP

(57) ABSTRACT

Injection port valves are generally discussed herein and more particularly to port valves that have a valve housing with a nozzle having an inlet opening, a body section, a skirt section, an interior cavity, and a valve seat at an intersection of the first nozzle and the body section in the interior cavity. A piston may be positioned within the interior cavity of the valve housing having a body section having an exterior surface, an upper piston section, a seal surface, and a piston cavity, and wherein the body section includes a wall layer that emits lubricant from within the wall layer to the exterior surface. A nut, which may be a Luer nut, having a flow passage in communication with a discharge nozzle having a discharge lumen may be attached to an end of the skirt section of the valve housing to thereafter connect to an infusion line. A spring can be positioned within the piston cavity and abutting against the nut, wherein when used, the spring being in a first position when the seal surface of the piston is abutted against the valve seat of the valve housing, and the spring being in a second position when the seal surface of the piston is separated from the valve seat.

24 Claims, 4 Drawing Sheets

U.S. PATENT DOCUMENTS

| | | | |
|---|---|---|---|
| 5,509,433 A | 4/1996 | Paradis | |
| 5,533,983 A | 7/1996 | Haining | |
| 5,535,785 A | 7/1996 | Werge et al. | |
| 5,540,661 A | 7/1996 | Tomisaka et al. | |
| 5,549,577 A | 8/1996 | Siegel et al. | |
| 5,569,235 A | 10/1996 | Ross et al. | |
| 5,573,516 A | 11/1996 | Tyner | |
| 5,584,808 A | 12/1996 | Healy | |
| 5,616,129 A | 4/1997 | Mayer | |
| 5,620,434 A | 4/1997 | Brony | |
| 5,624,414 A | 4/1997 | Boettger | |
| 5,645,538 A | 7/1997 | Richmond | |
| 5,674,206 A | 10/1997 | Allton et al. | |
| 5,676,346 A * | 10/1997 | Leinsing | 251/149.1 |
| 5,685,866 A | 11/1997 | Lopez | |
| 5,699,821 A | 12/1997 | Paradis | |
| 5,730,418 A | 3/1998 | Feith et al. | |
| 5,743,894 A | 4/1998 | Swisher | |
| RE35,841 E | 7/1998 | Frank et al. | |
| 5,782,816 A | 7/1998 | Werschmidt et al. | |
| 5,785,693 A | 7/1998 | Haining | |
| 5,788,215 A | 8/1998 | Ryan | |
| 5,806,551 A | 9/1998 | Meloul et al. | |
| 5,806,831 A | 9/1998 | Paradis | |
| 5,810,793 A | 9/1998 | Boettger | |
| 5,848,994 A | 12/1998 | Richmond | |
| 5,873,862 A | 2/1999 | Lopez | |
| 5,879,327 A | 3/1999 | Moreau DeFarges et al. | |
| 5,901,942 A | 5/1999 | Lopez | |
| 5,921,264 A | 7/1999 | Paradis | |
| 5,921,419 A | 7/1999 | Niedospial, Jr. et al. | |
| 5,928,204 A | 7/1999 | Lopez | |
| 5,957,898 A | 9/1999 | Jepson et al. | |
| 5,967,490 A | 10/1999 | Pike | |
| 6,029,946 A | 2/2000 | Doyle | |
| 6,036,171 A | 3/2000 | Weinheimer et al. | |
| 6,039,302 A | 3/2000 | Cote, Sr. et al. | |
| 6,040,366 A * | 3/2000 | Burkus et al. | 524/99 |
| 6,045,534 A | 4/2000 | Jacobsen et al. | |
| 6,063,062 A | 5/2000 | Paradis | |
| 6,068,011 A | 5/2000 | Paradis | |
| 6,106,502 A | 8/2000 | Richmond | |
| 6,113,068 A | 9/2000 | Ryan | |
| 6,117,114 A | 9/2000 | Paradis | |
| 6,127,320 A | 10/2000 | van Ooij et al. | |
| 6,132,403 A | 10/2000 | Lopez | |
| 6,142,446 A | 11/2000 | Leinsing | |
| 6,168,137 B1 | 1/2001 | Paradis | |
| 6,170,800 B1 | 1/2001 | Meloul et al. | |
| 6,228,069 B1 | 5/2001 | Barth et al. | |
| 6,245,048 B1 | 6/2001 | Fangrow, Jr. et al. | |
| 6,245,056 B1 | 6/2001 | Walker et al. | |
| 6,261,282 B1 | 7/2001 | Jepson et al. | |
| 6,273,869 B1 | 8/2001 | Vaillancourt | |
| 6,290,206 B1 | 9/2001 | Doyle | |
| 6,299,131 B1 | 10/2001 | Ryan | |
| 6,299,132 B1 | 10/2001 | Weinheimer et al. | |
| 6,344,033 B1 | 2/2002 | Jepson et al. | |
| 6,364,869 B1 | 4/2002 | Bonaldo | |
| 6,428,520 B1 | 8/2002 | Lopez et al. | |
| 6,482,188 B1 | 11/2002 | Rogers et al. | |
| 6,491,668 B1 | 12/2002 | Paradis | |
| 6,541,802 B2 | 4/2003 | Doyle | |
| RE38,145 E | 6/2003 | Lynn | |
| 6,572,592 B1 | 6/2003 | Lopez | |
| 6,616,627 B2 | 9/2003 | Willis et al. | |
| 6,626,418 B2 | 9/2003 | Kiehne | |
| 6,641,561 B1 | 11/2003 | Hill et al. | |
| 6,645,170 B2 | 11/2003 | Landau | |
| 6,669,673 B2 | 12/2003 | Lopez | |
| 6,669,681 B2 | 12/2003 | Jepson et al. | |
| 6,682,509 B2 | 1/2004 | Lopez | |
| 6,706,022 B1 | 3/2004 | Leinsing et al. | |
| 2003/0032940 A1 | 2/2003 | Doyle | |
| 2003/0060779 A1 | 3/2003 | Richmond | |
| 2003/0136932 A1 | 7/2003 | Doyle | |

\* cited by examiner

INJECTION PORT VALVE

Medical backcheck valves or injection port valves discussed herein generally relate to check valves for use with infusion lines and more specifically to needleless injection backcheck port valves that include pistons made from self-lubricated liquid silicone.

BACKGROUND

Needleless injection ports are frequently used in the medical industry for ready access to infusion lines. Broadly speaking, backcheck valves or needleless injection ports comprise quick-connect valves that permit medication or the like to be injected into infusion lines via a syringe and then close automatically when the syringe is withdrawn from the valve.

Representative prior U.S. Patents include U.S. Pat. Nos. 3,570,484, 3,831,629, 5,006,114, 5,049,128, 5,147,333, 5,201,725, 5,242,432, and 5,439,451. The contents of these patents are expressly incorporated herein by reference.

Regarding the needleless injection ports disclosed in U.S. Pat. No. 5,439,451, experience has shown that when a syringe is inserted into the injection port, the flexible elastomer piston 30 disclosed in the '451 patent occasionally sticks or does not readily re-seal upon withdrawing the syringe. Therefore, lubricant is typically added to the piston surface in the commercial embodiment to minimize friction between the piston 30 and the interior surface of the housing 10 to ensure proper seating of the main seal 68 and the conical shoulder 72 of the outer body 10 when the syringe is removed. However, adding a lubricant to the injection port involves an added step and negatively impacts the bottom line. In addition, the added step increases the risk of contamination to the valve and the risk of using a wrong lubricant.

Accordingly, there is a need for an improved piston that closes without the use of external lubricants.

SUMMARY

According to the present invention, there is provided an injection port valve comprising a piston positioned inside a valve housing, the piston comprises a wall surface that comprises fluids emitted from within the wall surface to the wall surface. A spring may be positioned inside an interior cavity of the piston to urge the piston in a first position or the piston may be made with sufficient resiliency to function in the absence of the spring. A Luer nut attached to an opening of the valve housing, the Luer nut comprising at least one flow passage and a discharge nozzle defining a port; and wherein the valve housing further comprises a first nozzle defining an inlet opening, and wherein the inlet opening, the at least one flow passage, and the port of the discharge nozzle are in fluid communication when a syringe tip is inserted into the inlet opening. Optionally, the valve housing may include a second nozzle, which makes the valve a Y-site.

According to another aspect of the present invention, there is provided a method for making an injection port valve comprising inserting a plug into an upper piston section of a piston to form a piston assembly, the piston comprising a body section having an exterior surface, an upper piston section, a seal surface, and a piston cavity. The piston may be made by mixing a two-part liquid silicone rubber material and injecting the mixed two-part liquid silicone rubber material into a mold, and wherein the body section comprises a wall thickness that emits a medical lubricant to the exterior surface of the piston. The piston assembly can be inserted into an interior cavity of a valve housing and the valve housing may comprise a cylinder end and a first discharge nozzle. A spring can also be inserted into the piston cavity with a nut installed thereafter, wherein the nut comprising at least one flow passage and a discharge nozzle proximate the cylinder end of the valve housing.

Other alternatives and embodiments for implementing the injection port valves in accordance with the practice of the present invention are also described herein and further discussed below in the Detailed Description section.

BRIEF DESCRIPTION OF THE DRAWINGS

These and other features and advantages of the present invention will become appreciated as the same becomes better understood with reference to the specification, claims and appended drawings wherein:

DETAILED DESCRIPTION

The detailed description set forth below in connection with the appended drawings is intended as a description of the presently preferred embodiments of the needleless injection port or backcheck valve (herein "valve") provided in accordance with the present invention and is not intended to represent the only forms in which the present invention may be constructed or utilized. The description sets forth the features and the steps for constructing and using the valve of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Figure 1:
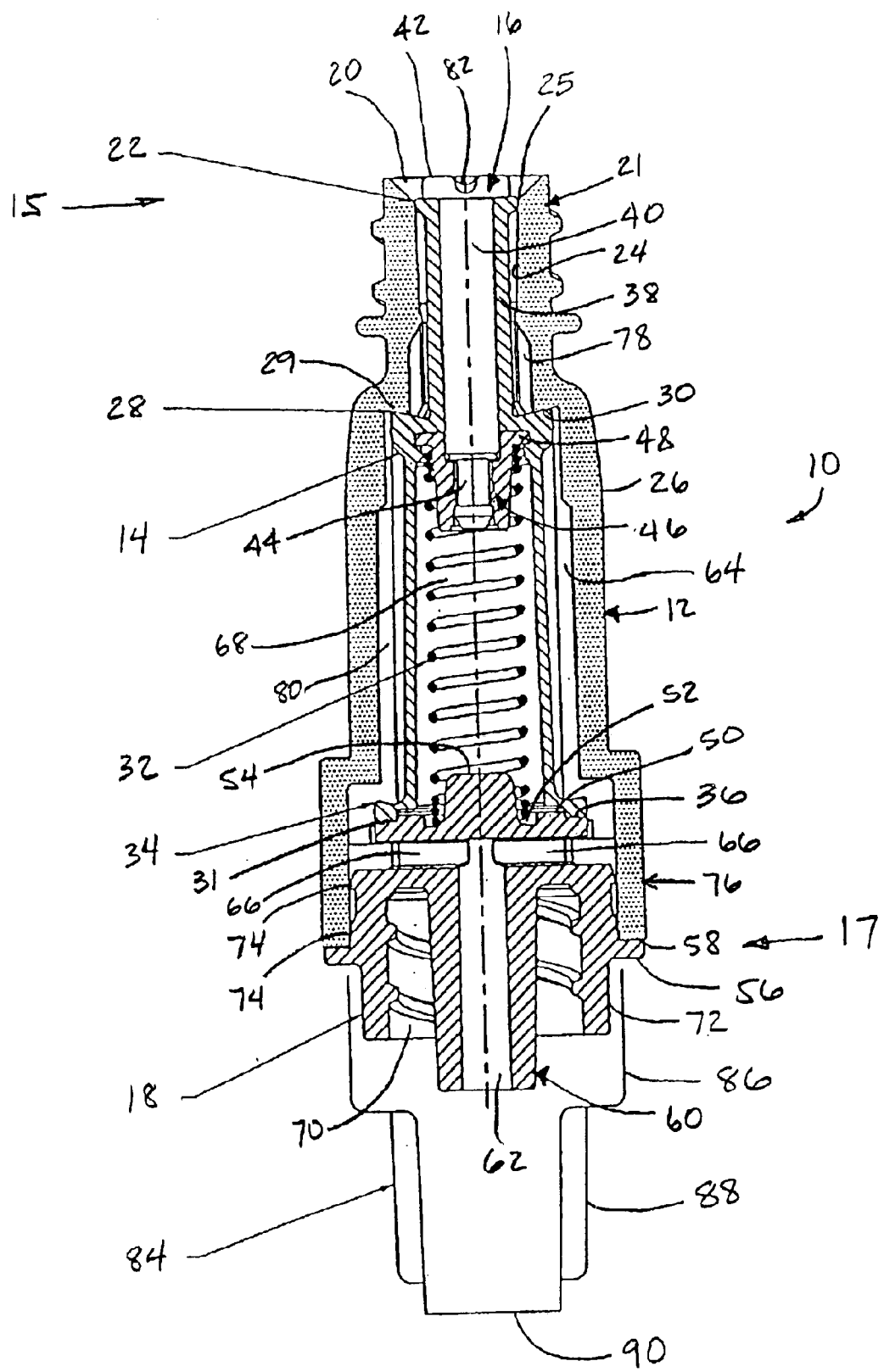
FIG. 1 is a semi-schematic cross-sectional side view of a needleless injection port valve provided in accordance to one practice of the present invention.

FIG. 1 shows a cross-section side view of a valve provided in accordance with practice of the present invention, which is generally designated 10. Generally speaking, the valve 10 comprises a housing 12, a piston 14 for opening and closing the fluid pathway from between the syringe S (not shown) and the infusion line (not shown), a rigid plug 16 to reinforce the piston and/or to facilitate actuation of the piston, and a nut fitting 18 configured to connect with an infusion line and serve as a conduit for the syringe S and the infusion line. The nut fitting 18 may be a Luer nut or may be a custom designed nut with flow passages and nozzles, as further discussed below.

The valve 10 is in the closed or sealed position when the piston 14 is in the natural uncompressed position shown in FIG. 1. In this sealed position, the valve 10 is sealed in a plurality of locations, which isolates the interior cavity of the valve from the exterior environment. At the inlet opening 20 of the nozzle 21, the upper seal 22 of the piston 14 is seated against the circumferential interior wall section 24 of the nozzle and the relative dimensions of the upper seal 22 and the diameter of the circumferential interior wall are such that the upper seal 22 is sufficiently compressed in the transverse direction to form a first seal point 25. For orientation purposes, the end near the nozzle 21 is the proximal end 15 and the end opposite the proximal end is the distal end 17.

Further distally from the inlet opening 20 at the juncture between the nozzle 21 and the housing mid-section 26, the middle seal 28 is seated against a shoulder 30. The cooperation between the middle seal 28 and the shoulder 30 provides a second seal point 29 for the valve assembly 10. Sufficient compression between the interface of the middle seal 28 and the shoulder 30 is provided by the spring force of the spring 32, which may vary depending on the spring constant chosen for the spring. Externally, the nozzle 21 may include a flat or smooth cylindrical surface (FIG. 3) or it may include male threads (FIG. 1) for engaging corresponding female threads on a lock collar of a syringe (not shown). As further discussed below, the force to sufficiently seal the valve 10 at the second seal point 29 may alternatively be imparted by the resiliency of the piston 14 in the absence of the spring 32. For example, by varying the blend of the piston material, varying the wall thickness of the piston, and/or changing the durometer, the piston 14 may expand to reseat at the second seal point 29 when a syringe S is removed without the spring.

Another sealing point is the seal 31 between the lower seal 34 of the piston 14 and the upper seal seat 36 of the nut 18. The seal 31 at this third location is adapted to seal the space occupied by the spring 32 from contamination by fluids dispensed from a syringe S (not shown) or from back flow, if any, from the infusion line. Although the three seal points 25, 29, 31 are discussed with specificity, more number or less number of seals may be incorporated in the valve 10 without deviating from the scope of the present invention.

The piston 14 may be made from a self-lube liquid silicone rubber, which is commercially available from Nusil Silicone Technology of Santa Barbara, Calif. The self-lube silicone rubber is a translucent, two-part system designed for liquid injection molding. When A and B components are mixed together, which are sold by Nusil Silicone Technology in a two-part kit, in equal portions, the liquid will cure to a tough, rubbery elastomer via addition-cure chemistry. After about sixty minutes of molding elapsed time, the cured silicone rubber will begin to self-lubricate a silicone fluid from within the wall to the piston surfaces. The fluid flows from within the wall to the interior and exterior surfaces of the piston 14 whenever the piston 14 is stressed or squeezed, such as when the piston 14 is compressed and released within the valve housing 12. As the piston 14 exudes lubricant to the surfaces, the mass or density of the piston reduces approximately an equal amount.

The fluid level or fluid flow to the surfaces can be adjusted with a formulation modification, such as by varying the ratio of component A and component B. Durometers available are 15, 30, 40, 50, and 60 with a range of high and low level of bleed out for each of the durometer range. In one embodiment, the piston has the following physical properties: about 1.15 specific gravity with a range of about 1.1 to about 1.2 being acceptable; a 50 durometer Shore A with an acceptable range of about 40 to about 60 durometer; at least 600 psi minimum tensile strength with about 800 psi minimum being more preferred; an elongation rating of about 275% minimum with about 350% minimum being more preferred; and a tear strength of about 100 ppi (pounds per inch) minimum with 125 ppi being more preferred.

Part A of the two-part component includes a noble metal catalyst based on platinum, although palladium and rhodium may be also be used. Part B of the two-part component includes a silicone hydride-functional cross-linker, polydimethyl siloxane polymer, and internal lubricant, which is medical grade fluorosilicone fluid. The two-part system is pumped directly into a mixer on an injection molding machine for homogenization and then directly into mold cavities. Vulcanization or curing occurs rapidly within the heated mold cavity, which is in the temperature range of about 245 to 485 degrees F.

Instead of liquid injection molding, a blend of high consistency silicone rubber may also be used to make the piston 14 using the same A/B materials discussed above. High consistency rubber may be mixed or blended together outside of a mold. A mill may be used for catalyzation of the two part components. The catalyzed material can pass through the mill several times until it is homogeneous then removed in sheet form. After milling, the material is cut or shaped into a preform that can be easily fed into a heated compression or transfer mold where the vulcanization takes place. The raw materials used in the present process are essentially the same as that used in the liquid silicone material except that a peroxide catalyst is used in the high consistency rubber.

The formed piston 14 has a consistency of a flexible or soft rubber and the like. As such, when the piston 14 is assembled inside the housing 12, the plug 16 is used to reinforce the upper piston section 38 of the piston. In particular, the upper stem section 40 of the plug 16, which is sized to fill the space of the upper piston section 38, is used to provide reinforcement for the upper piston section 38 of the piston 14. Alternatively, the piston 14 may be formed with a tough consistency having a resiliency that allows it to self-expand upon removal of the syringe S from the nozzle 21 without a spring. This may be accomplished, for example, by increasing the durometer of the piston material, varying the piston wall thickness along the length of the piston, and providing additional sealing points between the piston 14 and the interior cavity 64 of the housing 12.

The plug 16 is secured to the upper piston section 38 of the piston at the top by a head section 42 and at the bottom by attaching the plug tail 44 with a snap ring 46. The plug tail 44 and the snap ring 46 engage one another by way of a detent engagement, which may alternatively include friction engagement, adhesive, and the like. The snap ring 46 may be sized such that the spring 32 is capable of sliding over the snap ring and abut a flange section 48 of the snap ring. However, other engagement means, such as using a cylindrical ring, a threaded nut and the like to engage the plug, may be incorporated.

The piston 14 and the spring 32 are both in contact at their distal ends by the nut 18. The nut 18 includes an upper seal seat 36, as previously discussed, a raised floor 50 adjacent thereto, and a circular channel 52 for locating the distal end of the spring 32. A central projection 54 may be utilized to project into the central space of the spring 32 to assist in maintaining the alignment between the distal end of the spring and the circular channel 52. The nut 18 may be secured to the housing 12 via bonding the radially extending flange 56 to the perimeter end 58 of the housing. The bonding may include adhesive or bonding agent, may include sonic seal welding, and the like, such as a threaded engagement.

Figure 3:
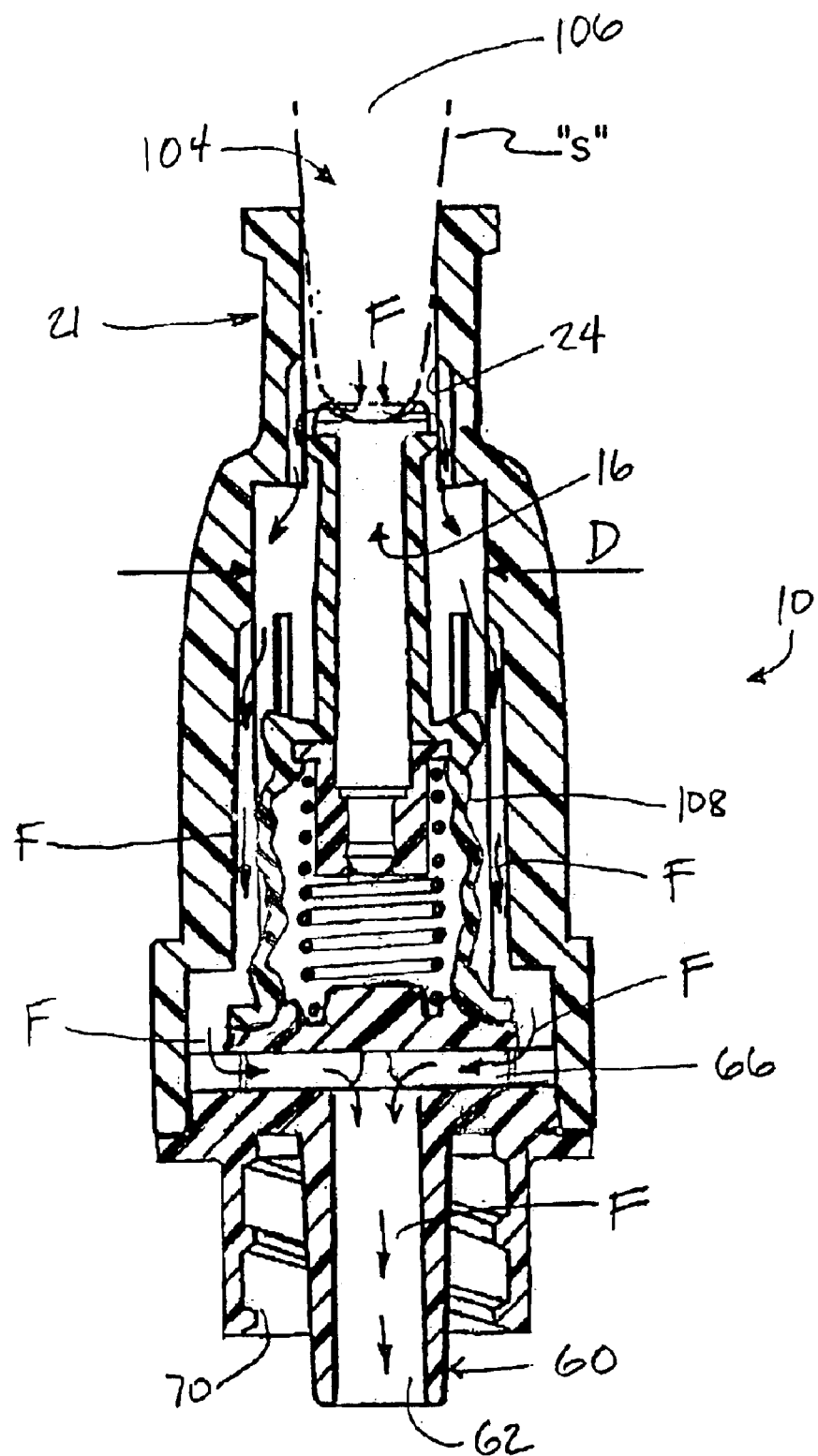
FIG. 3 is a semi-schematic cross-sectional side view of the valve of FIG. 1 in a compressed configuration.

A discharge nozzle 60, which defines a lumen or port 62, extends from the distal end of the nut 18. The lumen or port 62 is in communication with the interior cavity via two spaced apart liquid passages 66, with any number of liquid passages being suitable so long as friction loss is accounted for. The liquid passages 66 provide fluid pathways for fluids dispensed from a syringe S to travel and flow out of the nozzle 60, as further discussed below. The nut 18 further includes two optional vent holes (See, e.g., vent holes 116 in FIG. 4) for venting compressed gas trapped inside the spring chamber 68 when the chamber is compressed during a syringe insertion (FIG. 3). However, any number of vent holes are suitable so long as sufficient pressure drop is accounted for. The vent holes may be positioned anywhere along the raised floor 50 and extend through to the threaded skirt section 70 of the nut skirt 72. In the cross-sectional view shown, the vent holes may be positioned along the centerline of the valve 10, in between the two liquid passages 66. As readily apparent by a person of ordinary skill in the art, the vent holes and the liquid passages may be placed and adjusted depending on the particular numbers of each used. To assist in stabilizing the nut 18 to the housing 12, two spaced apart positioning members may be used to securely position the nut to the skirt 76 of the housing. Alternatively, the interface between the nut 18 and the skirt 76 of the housing 12 may be a threaded interface.

The valve 10 is preferably sized with standardized sizes. For example, the nozzle 21 and the threaded skirt section 70 may be made to attach with standard syringes and fittings for common medical applications, such as ISO standards 594/1 and 594-2 for Luer tapered fittings. The Nut 18, housing 12, plug 16, and snap ring 46 are preferably made from polycarbonate material in either clear, colored, and/or white finish, which may alternatively be made from nylon, polyethylene, polypropylene, acrylic, or their equivalents. The spring 32 is preferably made of stainless steel, such as a 316 or 302 stainless steel.

To facilitate fluid flow through the interior cavity 64 of the valve 10, upper flow channels 78 and lower flow channel 80 are incorporated. The upper flow channels 78 may include one or more channels and preferably comprises 4 to 12 channels and more preferably 8 channels. Similarly, the lower flow channels 80 may include one or more channels and preferably comprises 4 to 12 channels and more preferably 8 channels. Both the upper 78 and lower flow channels 80 are molded into the interior surface of the interior cavity 64. Thus when a syringe is inserted into the valve 10 to introduce fluids to the infusion line via the valve, the fluids may travel along the flow channels 78, 80 to the liquid passages 66 of the nut 18 and out the discharge nozzle 60. The channels 78, 80 are incorporated so that as the piston 14 is compressed by the syringe to expose the inlet opening 20 and the piston expands to block the interior cavity 64 of the housing 12, the channels provide open pathways for the fluids to flow through to the discharge nozzle 60.

The head section 42 of the plug 16 includes two plug flow channels 82 in a crucifix configuration. The flow channels are incorporated so that as the tip of the syringe is positioned against head section 42 of the plug 16, gaps are provided by the flow channels 82 to allow fluids to flow from the syringe. Alternatively, a plurality of parallel channels may be used or one wide channel instead of multiple smaller channels to accomplish the same flow function.

An optional valve cover 84 comprising a valve cover base 86 removably attached to the nut skirt 72 may be incorporated for sanitation, packaging, and/or shipping. The valve cover 84 may have a cylindrical shape or may have a tapered top section 88 and a closed top 90 as shown in FIG. 1.

Figure 2:
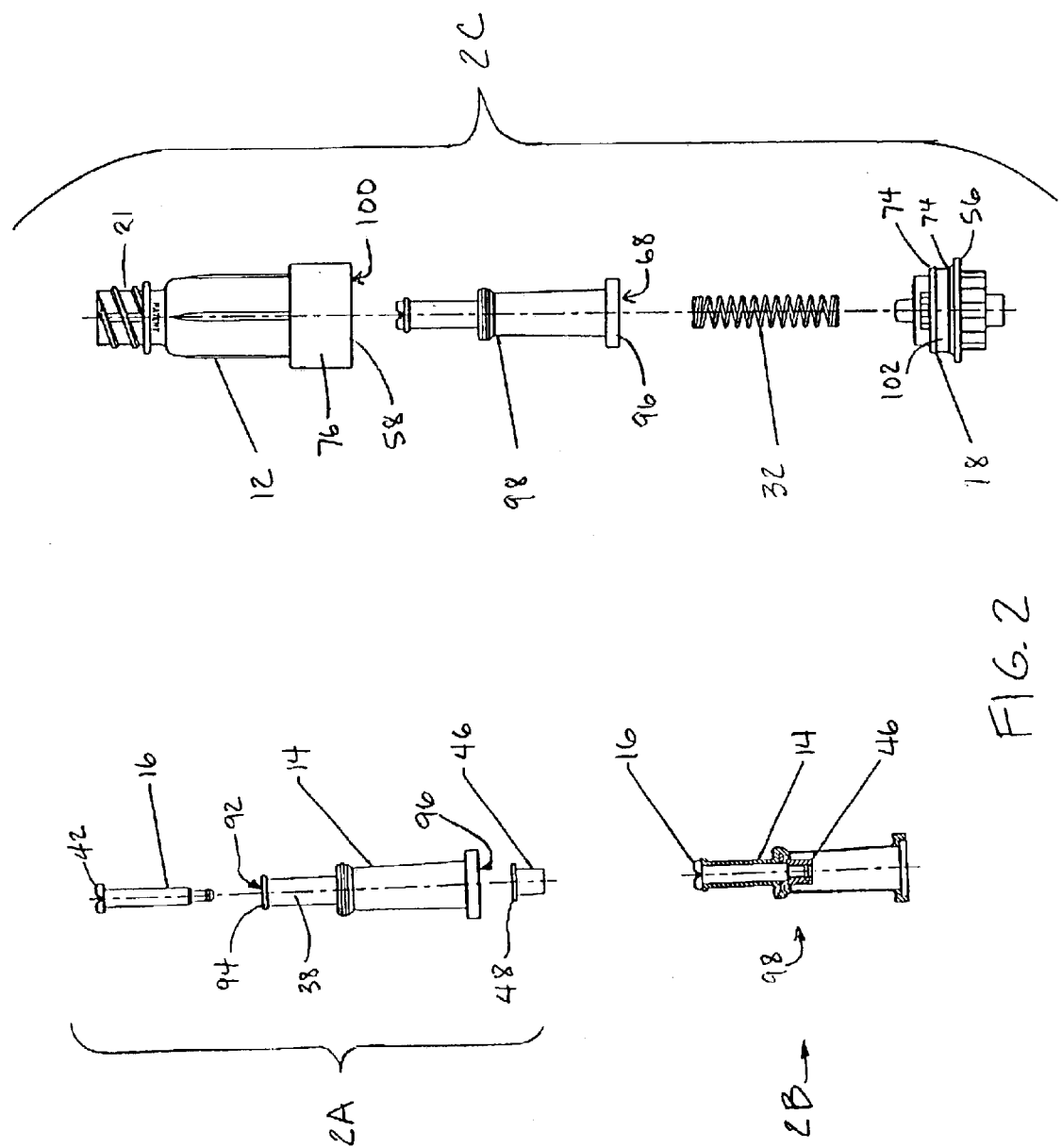
FIG. 2 is a semi-schematic exploded side view of the valve of FIG. 1.

Referring now to FIG. 2, there is shown a semi-schematic exploded side view of the valve 10 of FIG. 1. FIG. 2 depicts a method for assembling the various valve components. As shown, the valve 10 may be installed by inserting the plug 16 into the opening 92 of the upper piston section 38 of the piston 14 (2A). The plug 16 is completely inserted until the head section 42 of the plug and rests against the rim 94 of the upper piston section 38. The snap ring 46 is then inserted into the piston 14 via the lower opening 96 of the piston with the flange section 48 of the snap ring facing up (2A).

The assembled valve gut (2B) is then inserted into the valve body 12 (2C) by way of the lower opening 100 of the housing 12. A small tool (not shown), such as a plastic rod or a metal rod, may be used to assist in the insertion of the valve gut 98 into the valve housing and into the nozzle section 21 of the valve body. The spring 32 is then inserted into the spring chamber 68 of the piston by way of the lower opening 96 of the piston 14. Finally, the nut 18 is positioned at the lower opening 100 of the housing 12 so that the radially extending flange 56 abuts against the perimeter end 58 of the housing. The nut 18 may be bonded to the housing 12 by sonic welding, or by gluing.

Also shown is a pair of positioning members 74, which may include circumferential protuberances formed on the nut 18 to firmly position the nut 18 within the interior wall surface of the skirt 76 of the valve housing 12. Alternatively, instead of incorporating two or multiple positioning members 74, the entire mid-section 102 of the Nut 18 may be sized to firmly position within the interior wall surface of the skirt. Both the piston 14 and the valve housing 12 comprise a draft angle of about 0.3 degree to about 5 degrees. However, for purposes of the following disclosure, the term cylindrical housing section may be used, which is understood to include a piston or a valve body section that has a slight draft or tapered angle. In one embodiment, the draft angle of the piston 14 is 1 degree per side, the inside of the housing 12 body is 0.5 degree, and the female Luer taper 18 is 0.060 inch per inch.

Turning now to FIG. 3, the valve 10 is shown in the compressed or used position. As shown, a syringe S comprising a syringe tip 104 is inserted in the circumferential interior wall section 24 of the nozzle 21 to create a fluid pathway between the syringe fluid cavity 106 and the port 62 of the discharge nozzle 60. This is accomplished by exerting pressure on the plug 14 with the syringe tip 104, which in turn compresses the spring 32 and the piston 14 to separate the upper seal 22 and the middle seal 28 from the corresponding mating surfaces to separate the first seal joint 25 and the second seal joint 29, respectively. At this point, fluids F that exit the syringe tip 104, such as a therapeutic agent, a medicament and the like, may flow through the flow channels 82 located in the head section 42 of the plug 16, then through the interior cavity 64 of the valve housing 12.

The interior cavity 64 includes an interior cavity diameter D. In the normal uncompressed position (FIG. 1), the piston 14 has a cross-sectional diameter that is less than D. However, as the piston 14 is activated or compressed by the syringe S (FIG. 3), the piston wall 108 crumbles and compresses in reaction thereto. Since the piston 14 is preferably practiced without pre-formed crumble zones or regions along the piston wall, the piston wall randomly crumbles and collapses with certain portions of the wall expanding and certain portions of the wall collapsing in unpredictable fashions.

The portions of the piston wall 108 that expand to contact the cavity diameter D would normally obstruct the fluids F flowing from the syringe S. However, because the interior cavity 64 includes lower flow channels 80, the obstruction is mitigated as the channels provide open passages for the fluids F. The same is true for the upper flow channels 78 located in the nozzle section 21 of the valve housing 12. Once the fluids F flow past the upper channels 78 and the lower channels 80, they flow into the plurality of liquid passages 66 located in the nut 18 and then out the port 62 of the discharge nozzle 60. Although not shown, fluids that leave the discharge nozzle 60 flow into an infusion line connected to the threaded skirt section 70 of the valve 10.

Upon completing the infusion process and removal of the syringe S from the nozzle 21, the spring 32 releases to expand the piston 14, which then causes the first and second seal joints 25, 29 to be reestablished. As the piston 14 is formed from a self-lubricated silicone material, little resistance or friction is encountered during the expansion process. As previously discussed, liquid silicone exudes to the surface of the piston 14 to minimize friction between the interface of the piston and the valve housing 12. The valve 10, thus, provides a quick access injection site that is reliable and safe to use.

Figure 4:
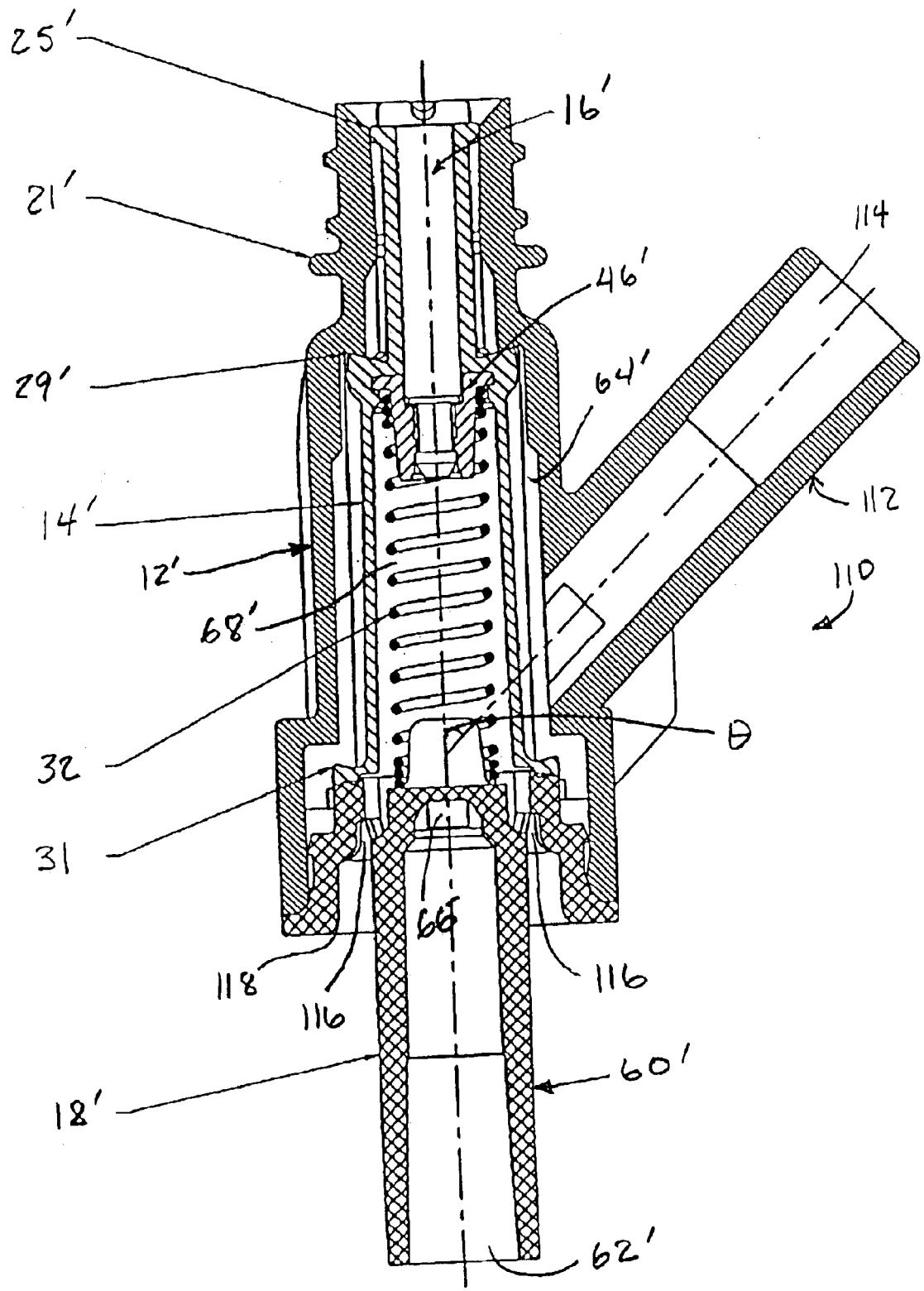
FIG. 4 is a semi-schematic cross-sectional side view of an alternative needleless injection port valve provided in accordance to another practice of the present invention.

Turning now to FIG. 4, there is shown an alternative valve embodiment provided in accordance to another practice of the invention, which is generally designated 110. Like the valve 10 of FIG. 1, the alternative valve 110 also functions as a needleless injection port. The valve 110 comprises essentially the same components as the valve 10 of FIG. 1 with a few exceptions. For example, the valve 110 includes a valve housing 12', a piston 14' made from the same self-lubricated silicone, a plug 16', a spring 32', a snap ring 46', and a nut 18'. The valve 110 also includes a plurality of seal joints, including a first seal joint 25', a second seal joint 29', and a third seal joint 31'. However, the nut 18' has been modified to accept a friction fit fitting (not shown) and the valve housing 12' has been modified to function as a Y-site, i.e., it has two inlets and one outlet. Also shown in FIG. 4 is a pair of optional vent holes 116 for venting entrapped gas from the spring chamber 68'. The optional vent holes 116 are similar to the optional vent holes discussed above for the valve 10 in FIG. 1.

In the embodiment shown, the valve housing 12' includes a second nozzle 112 extending from a side of the housing. The second nozzle 112 includes a nozzle axis that is positioned at an angle θ from the axis of the first nozzle 21', which may range anywhere from about 10 to about 90, with about 25 to about 65 being more preferred. The second nozzle 112 defines a port or lumen 114 that is in communication with the port or lumen 62' of the discharge nozzle 60' via the interior cavity 64' and the liquid passages 66' located in the nut 18'. In practice, the second nozzle 112 is preferably used for IV infusion, such as for hooking to a salient solution container, and the first nozzle 21' is preferably used for introducing supplemental medication or other fluids. Thus, while the first nozzle 21' includes a plurality of seal joints for sealing the valve 110 from the exterior environment, the second nozzle 112 has a constant open configuration with the port 62' of the discharge nozzle 60'. In other words, during infusion of fluids into the valve 110 from a syringe S (not shown) via the first nozzle 21', solutions or fluids may also flow into the valve 110 from the second nozzle 112.

The nut 18' is shown with a threadless skirt section 118 and a discharge nozzle length that is longer relative to the discharge nozzle length of the nut 18 of FIG. 1. This modified nut configuration is adapted to frictionally engage an infusion line rather than threading to a fitting to provide a relatively quicker connect/disconnect with the infusion line. The modified configuration may be used by sliding an open end of the infusion line over the discharge nozzle 60' until the end of the infusion line engages the threadless skirt section 118. Alternatively, a pre-assembled infusion line may be incorporated with the valve 110 by assembling an infusion line over the discharge nozzle 60' and solvent bond the connection. However, the nut 18 from FIG. 1 may be incorporated in the present embodiment as well without deviating from the scope of the present invention.

Although the preferred embodiments of the invention have been described with some specificity, the description and drawings set forth herein are not intended to be delimiting, and persons of ordinary skill in the art will understand that various modifications may be made to the embodiments discussed herein without departing from the scope of the invention, and all such changes and modifications are intended to be encompassed within the appended claims. Various changes to the valves may be made including manufacturing the dimensions differently, using different materials, changing the interface between the various components to include ridges and channels, etc. For example, instead of having flat seal joints, the surfaces may be serrated, the number of flow channels may be modified, and the snap ring may simply be a cylindrical ring. Other changes may include incorporating a smooth inlet nozzle instead of a threaded nozzle, adding colors to the valve finishes, changing the shape of the housing and of the piston, and using the valve in non-medical related industries, such as in food processing, chemical processing, etc. Still alternatively, other medical lubricant may be used instead of liquid silicone to lubricate the piston surfaces and using similar blend or mixture to create a piston wall that exudes medical lubricant from inside the wall to the wall surfaces. Accordingly, many alterations and modifications may be made by those having ordinary skill in the art without deviating from the spirit and scope of the invention.

What is claimed is:

1. An injection port valve comprising:
   a valve housing comprising a first nozzle having an inlet opening, a body section, a skirt section, an interior cavity, and a valve seat located in the interior cavity;
   a piston positioned within the interior cavity of the valve housing, the piston comprising a body section having an exterior surface, a seal surface, and a piston cavity, wherein the body section comprises a wall layer that emits liquid silicone from within the wall layer to the exterior surface, and wherein the seal surface is abutted against the valve seat of the valve housing;
   a nut comprising a flow passage in communication with a discharge nozzle comprising a discharge lumen attached to an end of the skirt section of the valve housing; and
   wherein the inlet opening of the first nozzle is in fluid communication with the discharge lumen of the discharge nozzle when the seal surface is spaced apart from the valve seat.

2. The valve of claim 1, wherein the first nozzle comprises male threads.

3. The valve of claim 1, further comprising a plug and a spirng positioned in the piston cavity of the piston.

4. The valve of claim 3, wherein the plug comprises a head section and wherein the head section comprises a plurality of flow channels.

5. The valve of claim 1, wherein the nut is a Luer nut.

6. The valve of claim 1, wherein the nut comprises a skirt section, and wherein the skirt section and the discharge nozzle cooperate to engage an infusion line.

7. The valve of claim 1, further comprising a second nozzle having a second inlet opening and a second nozzle axis, and wherein the second nozzle axis is positioned at angle of about 25 degrees to about 65 degrees from a first axis of the first nozzle.

8. The valve of claim 7, wherein the second nozzle defines a second lumen and wherein the second lumen is in liquid communication with the discharge lumen of the discharge nozzle.

9. The valve of claim 1, wherein the nut further comprises a radially extending flange, and wherein the radially extending flange is welded to the end of the skirt section.

10. The valve of claim 1, wherein the interior cavity of the valve housing comprises a plurality of flow channels.

11. The valve of claim 1, further comprising a resilient member positioned within the piston cavity, and wherein the resilient member biases the seal surface of the piston against the valve seat of the valve housing.

12. The valve of claim 1, wherein the piston comprises an interior surface and wherein the wall layer emits liquid silicone from within the wall layer to the interior surface.

13. An injection port valve comprising:
   a piston positioned inside a valve housing, the piston comprises a wall having a wall surface that emits medical lubricant from within the wall to the wall surface when the piston is compressed;
   a Luer nut attached to an opening of the valve housing, the Luer nut comprising a flow passage and a discharge nozzle defining a port; and
   wherein the valve housing further comprises a first nozzle defining an inlet opening, and wherein the inlet opening, the flow passage, and the port of the discharge nozzle are in fluid communication when a syringe tip is inserted into the inlet opening.

14. The valve of claim 13, wherein the piston is made by injection molding a two-part liquid silicone rubber material into a mold.

15. The valve of claim 13, wherein the piston is made by the process of forming a homogeneous sheet silicone and then cutting and forming a section of the homogeneous sheet that can be fed into a heated compression or a transfer mold.

16. The valve of claim 13, wherein the first nozzle comprises male threads.

17. The valve of claim 13, wherein the Luer nut comprises a threaded skirt section.

18. The valve of claim 13, further comprising a second nozzle positioned at an angle relative to the first nozzle.

19. The valve of claim 18, wherein the second nozzle is in constant fluid communication with the port of the discharge nozzle.

20. The valve of claim 13, wherein the inside of the valve housing comprises a plurality of flow channels.

21. The valve of claim 13, wherein the inside of the valve housing comprises a first set of upper flow channels and a second different set of lower flow channels.

22. The valve of claim 13, further comprising a spring positioned within an interior piston cavity.

23. The valve of claim 13, wherein the medical lubricant comprises liquid silicone.

24. The valve of claim 13, wherein the Luer nut comprises a second flow passage.

* * * * *

UNITED STATES PATENT AND TRADEMARK OFFICE
CERTIFICATE OF CORRECTION

PATENT NO. : 6,871,838 B2 Page 1 of 1
DATED : March 29, 2005
INVENTOR(S) : Raines et al.

It is certified that error appears in the above-identified patent and that said Letters Patent is hereby corrected as shown below:

<u>Title page,</u>
Item [56], References Cited, U.S. PATENT DOCUMENTS,
delete "5,251,873 A    5/1995", insert -- 5,251,873 B1    5/1995 --; and
"6,040,366" reference, delete "Burkus et al.", insert -- Burkus, II et al. --.

<u>Column 8,</u>
Line 59, delete "spirng", insert -- spring --.

<u>Column 9,</u>
Line 4, before "angle", insert -- an --.

Signed and Sealed this

Twenty-eighth Day of March, 2006

JON W. DUDAS
*Director of the United States Patent and Trademark Office*